United States Patent [19]

Hata

[11] Patent Number: 4,879,238

[45] Date of Patent: Nov. 7, 1989

[54] DEODORANT AND METHOD FOR PREPARING AND STORING SAME

[75] Inventor: Kosei Hata, Osaka, Japan

[73] Assignee: Seikenkai, Japan

[21] Appl. No.: 604,417

[22] Filed: Apr. 30, 1984

Related U.S. Application Data

[63] Continuation of Ser. No. 260,487, May 4, 1981, abandoned, which is a continuation of Ser. No. 799,319, May 23, 1977, abandoned.

[51] Int. Cl.$^4$ .................. C12N 1/38; C12N 1/36; C12N 1/20
[52] U.S. Cl. .................... 435/244; 435/245; 435/260; 435/252.1; 435/253.6; 424/93; 424/76.6
[58] Field of Search ............... 435/172, 244, 245, 253, 435/260, 264, 267, 268, 172.1; 424/76, 93; 71/6, 8–10; 210/601

[56] References Cited

U.S. PATENT DOCUMENTS

| | | | |
|---|---|---|---|
| 1,918,053 | 4/1931 | Nitardy et al. | 435/260 |
| 3,376,219 | 4/1968 | Silvey | 424/76 |
| 3,813,316 | 5/1974 | Chakrabarty | 435/172 |
| 3,957,974 | 5/1976 | Hata | 424/93 |
| 4,345,032 | 8/1982 | Hata | 435/253 |
| 4,492,756 | 1/1985 | Ghisalba et al. | 435/253 |
| 4,518,696 | 5/1985 | Gehrman et al. | 435/253 |
| 4,579,734 | 4/1986 | Hata et al. | 424/93 |

FOREIGN PATENT DOCUMENTS

| | | |
|---|---|---|
| 1040278 | 8/1966 | United Kingdom . |
| 1061894 | 3/1967 | United Kingdom . |
| 1167196 | 10/1969 | United Kingdom . |
| 1190386 | 5/1970 | United Kingdom . |
| 1251483 | 10/1981 | United Kingdom . |

OTHER PUBLICATIONS

Mitic, Transformation of Amino Acid Composition in Bacterial Cells of *Lactobacillus Bulgaricus*, *Chem. Abst.*, vol. 85, p. 333, 1976.

Benedict et al, Preservation of Microorganisms by Freeze-Drying, *App. Microbiol*, vol. 6, No. 6, (1958), pp. 401–407.

Chem. Abs., 85:17012h (1976).

Davis et al., *Microbiology*, 2nd Ed., Harper & Row, N.Y., 1973, pp. 53–55.

Bergey's Manual of Determinative Bacteriology, 8th Ed., Williams & Wilkins, Baltimore, 1974, pp. 451–471.

Chemical Abstracts 87:37379c (1977).

Chemical Abstracts 82:110473g (1975).

Chemical Abstracts 86:187707b (1977).

*Primary Examiner*—Esther M. Kepplinger
*Attorney, Agent, or Firm*—Sughrue, Mion, Zinn, Macpeak, and Seas

[57] ABSTRACT

The present invention relates to the deodorization of foul-smelling substances by the use of a single strain or a few strains of autotropic bacteria.

29 Claims, 1 Drawing Sheet

DEODORANT AND METHOD FOR PREPARING AND STORING SAME

This application is a continuation, of application Ser. No. 260,487, filed May 4, 1981, now abandoned which is in turn a continuation of application Ser. No. 799,319, filed May 23, 1977, now abandoned.

BACKGROUND OF THE INVENTION

Certain deodorants comprising deodorizing strains of bacteria have been hitherto commercially available, however, such deodirants were of doubtful efficacy and created problems, especially in storage, etc.

BRIEF SUMMARY OF THE INVENTION

The present invention relates to the deodorization of foul-smelling substances by the use of a single strain or a few strains of autotrophic bacteria.

The deodorants of the present invention differ from those of the prior art in the number of strains of bacteria to be used for deodorization, in the method of cultivation of the bacteria and also in the method of preservation of deodorizing ability of the bacteria.

Thus, after a series of analytical, systematic, original studies on the removal of foul odors originating from living things, the present inventor has succeeded in finding a basic principle for the deodorization with microorganisms as will be explained in detail below:

Further, the inventor has succeeded in effectively using small number of strains of bacteria or single strain for deodorization, which has hitherto been considered to be impossible from a theoretical standpoint.

This is a beneficial result of the basic principles developed by the present inventor.

Furthermore, from these successes, it has become possible to establish a method of culturing the bacteria so as to permit them to retain their original deodorizing power in the course of repeated subculture. Further, a method of storage of such bacteria for a long period of time has been developed.

It is also now possible to investigate the nonpathogenicity of such bacteria which hitherto, has been difficult.

BRIEF DESCRIPTION OF THE DRAWINGS

The attached figures show typical examples of growth of bacteria cultivated in three media different in levels of nutrition, such as high, medium and low, which growth is further accelerated by the addition of substances containing S, N and C in various concentrations, when the multiplication of the bacteria reaches a logarithmic phase.

In the above Figure, the concentration of said substances were as follows.

⓪: the substances containing S, N and C were not added.

①: each of $Na_2S$, $NH_3$ and acetic acid was added in 0.1 g.

②: each of $Na_2S$, $NH_3$ and acetic acid was added in 1 g.

③: each of $Na_2S$, $NH_3$ and acetic acid was added in 2 g.

DETAILED DESCRIPTION OF THE INVENTION

Attempts to deodorize excrement using microorganisms have often been made and among them, some microorganisms were commercialized on a temporary basis. However, it was a general phenomenon that they disappeared from the market soon afterwards. The reason why they were abondoned after a short period of commercial production is considered to be due to ⓐ their poor ability to effect deodorization, ⓑ difficult conditions for their cultivation, ⓒ the difficulty in storing them for rather a long period while retaining their original high ability to deodorize, ⓓ the lack of information on their non-pathogenicity and ⓔ lack of economy. The present inventor has succeeded in deodorizing excrement using only one species of a strain or a very small number of species of strains and obtained much original information on the deodorization itself and also on bacteria having an ability to deodorize. Thus, the present inventor has succeeded in overcoming various problems in the dedorization of the excrement including ⓐ-ⓔ mentioned above.

Generally speaking, it is difficult to establish a general theory for the deodorization of foul-smelling substances from the stand-point of their composition and chemical structures. Moreover, it should be pointed out that the composition of foul-smelling substances, such as excrement, is very complicated because of the number of compounds contained in an excrement is almost infinite since, at first, food or fodder as a raw material for the excrement consists of many kinds of materials and secondly, it is a final product obtained after many or an almost infinite number of biochemical reactions induced by enteric bacteria existed in the intestines. This in turn affects the production of foul-smelling compounds contained in the excrement. Therefore, even if only the foul-smelling components in the excrement resulting from metabolism are considered, the number of such compounds is very much large yet thin proportions are very small. The situation is further complicated by reactions with various non-odoriferous components.

As mentioned above, since the excrement is a product of such complicated biochemical reactions, it is almost impossible to develop a general theory for the deodorization. Moreover, in fresh excrement, since there exist so many bacteria, e.g. $10^{11}$ per 1 g of the excrement, wherein almost all are enteric bacteria, many kinds of reaction products of metabolism are continuously produced. Furthermore, among those enteric bacteria, there exist many hardy bacteria such as colon bacilli and spore-forming bacilli. Therefore, unfortunately, it is impossible to carry out a sufficient deodorization test on the total foul-smelling compounds existing in the excrement to establish an effective deodorization method and moreover it is also impossible to find a method to remove the bad-smelling products of metabolism which are produced one after another successively in the excrement exhausted from the human body.

For such reasons, the present inventor concentrated his efforts in the deodorization study of the excrement on S-containing compounds, N-containing compounds and C-containing compounds existing in the excrement. However, unfortunately, it was found that, even if the study is restricted to those three groups if compounds mentioned above, it is almost impossible to carry out a sufficient test on each compound belonging to those groups and get a reliable conclusion since there exist so many kinds of compounds belonging to each group. For example, ⓐ the removal of foul order due to the existence of S-containing compounds was tested using so-called sulfur bacteria. It is surely true that there exist many bacteria which attack S-containing compounds and they are called sulfur bacteria in short, however, their behavior and activity to S-containing compounds are very much different from each other and moreover, unfortunately, in the excrement, so many kinds of S-containing compounds are present.

Accordingly, after many experiments had been carried out by the present inventor, progress has been realized but further problems remain on the interaction between sulfur bacteria and the S-containing compounds in the excrement. Furthermore, ⓑ on the removal of foul odor due to the existence of N-containing compounds using nitration bacteria, it was also confirmed that a complete study supported by a sufficient experimental test can never be accomplished. And moreover, ⓒ the condition was the same also on the C-containing compounds since there exist many compounds whose main component is the carbon atom and a sufficient tests can never be expected even if the test is restricted on the decarboxylation.

Thus, it was confirmed that any reliable conclusion on the deodorization of the excrement can never be derived experimentally, even if the experimental test is concentrated on the three groups of compounds mentioned above.

In view of such difficulties in the study of the deodorization as mentioned above, the present inventor has attempted to find, at first, one or two representative foul-smelling compounds belonging to the same group defined above. Fortunately, it was found that ⓐ sodium sulfide is representative of the group of compounds having an S-atom in their molecules and accordingly, when any bacterium which effectively act on to sodium sulfide to assimilate or modify it chemically into completely odorless material (hereafter, such an action will be called as S-action in short), is found, progress towards the solution of deodorization problem concerning the existence of foul S-containing compounds can be considered to be made; ⓑ on the group of compounds having the N-atom in their molecules, ammonia, indole or skatole and representative of the group and the next step is to find suitable bacterium having ability to render odorless such representative compound (N-action). ⓒ any lower aliphatic carboxylic acid can be representavive of the group of compounds having the C-atom in their molecules, and, of course, to find a proper bacterium (C-action) is the next step. That is, through an extensive experimental study carried out using many combinations of various organic reagents and strains, it was found that although there exist many S-containing compounds in the excrement such as $SO_2$, $CS_2$, $CH_3SH$, . . . , $(C_6H_5CH_2)SH$, etc., together with $H_2S$ and $Na_2S.9H_2O$ as the typical examples known to be existant in the excrement, it is unnecessary to examine the behavior of a bacterium on to those sulfide compounds one by one if sodium sulfide is representative of those sulfur compounds and the same will be true also on the nitrogen compounds and the carbon compounds as explained already. By following the procedure established by the inventor, a practical deorization test can be carried out using bacteria of single strain if they exhibit (a) S-action (as explained above, this action can be confirmed experimentally using $Na_2S$ as the representative material to be tested), (b) N-action (this action can be tested using $NH_3$, indole or skatole as the representative of N-compounds) and (c) C-action (this can be tested by using any one of lower alphatic carboxylic acids) simultaneously, or by using a plural number of strains of bacteria if those strains act in a different way from each other. Thus, this procedure makes it easy to establish a method for deodorization. Furthermore, the present inventor has found that there is a special relationship between the deodorization bacteria and those S-, N- and C-containing compounds as will be explained later. The obtained conclusion on the general procedure to find how to deodorize the excrement will be called the S.N.C. theory. However, it should be pointed out that the deodorization of the excrement is not as simple as selecting a suitable strain or strains. The determination of other required conditions for the deodorization is also necessary. (I) At first, a comment will be made on the species of bacteria which will be used in the present invention. The present inventor decided to limit the choice the bacteria to autotrophic bacteria, since autotrophic bacteria have an ability to take their nutrition effectively from a medium of low nutrition and to assimilate it into their own bodies. This means the nutritional demand of the bacteria is rather low.

(II) Hitherto, as already reported in publications, it is known that thio-bacilli which are autotrophic bacteria, have an ability to remove a foul odor due to the existence of mercaptan. However, since the bacilli had a fatal defect from the commercial stand-point, i.e., that the rate of multiplication of the bacilli is very low, they have not yet been put to practical use for the deodorization of excrement. In the course of the study, it was necessary for the present inventor to either abandon this group of bacteria for the reason that their rate of multiplication is low or to endeavor to find a strain belonging to this group of bacteria which has an appreciable rate of multiplication. The problem of velocity of multiplication of bacteria raises two other problems: (1) is it possible for the given bacteria to overcome other various bacteria in its struggle for existence in the excrement ? and (2) is mass production possible ?

(III) Even if a bacterium has a rapid rate of growth under ordinary conditions, it is doubtful that the bacterium have the ability to realize a high rate of multiplication in the excrement since it contains a certain amount of gall which has a strong ability to prevent the multiplication of bacteria. It is known generally that the growth of bacteria living in the earth is rapidly prevented by the existence of about 0.5% of powder of gall. Since autotrophic bacteria belong to the group of bacteria living in the earth, they are, accordingly, very sensitive to gall.

Therefore, for the purpose of the present invention, it was necessary matter to find a strain which is not sensitive to gall or to acclimatize a strain to be resistant to gall in more than 1% concentration.

(IV) As a necessary property of bacteria to be used in the present invention, the bacteria should have the ability to multiply rapidly or rapidly suppress the growth of other bacteria for a long period not only in aerobic conditions but also in the condition where the partial pressure of oxygen is rather too low when the passing of air through the medium is not carried out, since the inner part of the excrement is considered to be in a highly anaerobic condition due to the existence of living bacteria in the excrement.

Furthermore, the pH value of the environment of the excrement rapidly fluctuates and the bacteria which are applicable for the present purpose should have the ability to resist such a pH change.

(V) Since the excrement is, generally, a mixture of feces and urine, the bacteria to be used for the present purpose should have a high activity even in such a medium where the concentration of salt is very high.

(VI) The bacteria to be used for the present purpose should not cause disease in animals and plants. This is a very severe condition to be maintained for the bacteria used for the deodorization.

The bacteria which can be used for the deodorization of the excrement should have these properties.

Here, a question arises, is it possible that any one strain of bacteria can have all of these properties, mentioned above, at the same time, as the necessary condition for a deodorizing substance. It has been considered to be a very difficult matter to provide a strain of bacteria having an ability to simultaneously convert S-, N- and C-containing compounds into non-smelling substances. Again, such ability is only one of the said necessary conditions for the deodorizer; said deodorizer should have other many properties in order to play the role satisfactorily, as mentioned above.

The present inventor has succeeded in isolating various bacteria each having the characteristic properties, from among many types of bacteria. For example, some of those isolated species only exhibited S-action or N-action or C-action, some exhibited two of those three actions and some exhibited three actions together at the same time, wherein those isolated strains satisfied the conditions (II)–(VI) mentioned above. Using those isolated strains, accordingly, the correctness of the S.N.C-theory of the present inventors was able to be proven. In Table 1, an example of such experimental data is listed. Table 1 lists cases where combination of three species of strains, F.R.I. No. 2546, No. 2545 and No. 2544, each having an ability to exhibit one different action, strongly, was used, or a case where only one strain, F.R.I. No. 2823, having an ability to exhibit S-, N- and C-actions simultaneously was used, from Table 1, it is clearly understood that, in order to carry out the deodorization effectively, it is necessary to satisfy the condition that bacteria, regardless of whether they consist of only one strain or of multiple strains, should have an ability to take said three actions simultaneously.

TABLE 1

| Characteristic in Action | F.R.I. No. | Residual Odor Degree (Deodorizing power test) after standing for each given period at 28° C. | | |
|---|---|---|---|---|
| | | 24 hr | 48 hr | 72 hr |
| S-action is especially strong | 2546 | 2 | 1' | 1 |
| N-action | 2545 | 3 | 3 | 3 |
| C-action especially strong | 2544 | 3 | 3 | 2' |
| S + N-actions are especially strong | 2546 + 2545 | 1' | 1' | 0' |
| S + C-actions are especially strong | 2546 + 2544 | 1' | 1' | 0' |

TABLE 1-continued

| Characteristic in Action | F.R.I. No. | Residual Odor Degree (Deodorizing power test) after standing for each given period at 28° C. | | |
|---|---|---|---|---|
| | | 24 hr | 48 hr | 72 hr |
| N + C-actions are especially strong | 2545 + 2544 | 3 | 2' | 2 |
| S + N + C-actions, all together | 2546 + 2545 + 2544 | 1' | 1' | 0' |
| S + N + C-actions, all together | 2823 | 0 ~ 1 | 0' | 0 ~ 0' |

Remarks:
① In each test, 10 wt % of culture liquor was added to an excrement based upon the weight of the excrement.
② F.R.I. No. means the acceptance number of the Fermentation Research Institute (Agency of Industrial Science & Technology-Japan).
③ The deodorization power was indicated with residual odor degree, wherein
0 ... completely deodorized (the most effective),
0' ... it was not certain the foul odor had disappeared.
1 ... at first, it was possible to detect a faint odor, however, instantly, it became untakeable.
1' ... at first, it was surely possible to detect a faint odor, however, soon after, it became impossible to detect.
2 ... a faint odor, however, it was possible to detect with certainty.
2' ... the residual odor was much weaker than the foul odor of the control sample (equal to the test sample).
3 ... the residual odor was weaker than the foul odor of the control sample.
3' ... a little weaker than the foul odor of the control sample,
4 ... almost equivalent to the foul odor of the control sample (however it should be pointed out that even if the degrees of odor in both samples were equivalent, it doesn't mean the amounts of substances having foul odor in both samples are equivalent to each other).

Next, there will be described in detail the biochemical properties and the biological characteristics of four typical strains of bacteria, that is, a strain having an ability to simultaneously exhibit S-, N- and C-actions (that is, F.R.I. No. 2823) and three strains, wherein two of them can exhibit one action especially strongly such as S-action (F.R.I. No. 2546 or C-action (F.R.I. No. 2544) and the other exhibits only N-action (F.R.I. No. 2545). These strains were used very often for the experimental tests for the establishment of the deodorization theory of the present inventor.

Table 2 shows the results of microscopic test of those four strains of bacteria and also their biochemical behavior, Table 3 shows their abilities to decompose various saccharides, Table 4 shows the effect of nutrition on their multiplication and also the results of tests to accelerate their growth and Table 5 shows the results of cultivation of those four bacteria when various effective components contained in the excrement were added into various culture media as nutriments. As it can be understood from Table 5, the rate of growth of those bacteria is accelerated by the addition of nutriments such as S-, N- and C-containing substances into a basic culture medium, if the medium consists of poor nutriments, however, with the increase of nutrition in a basic medium, such addition becomes ineffective for the acceleration of the rate of growth. That is, when a basic culture medium of medium nutrition was used for cultivation, a weak acceleration was observed by the addition of those substances and again, when a basic culture medium of high nutrition was used, an even weaker acceleration was barely observed by an accurate measurement using a nephelometer, it was impossible to observe this with the naked eye.

Figure 1:
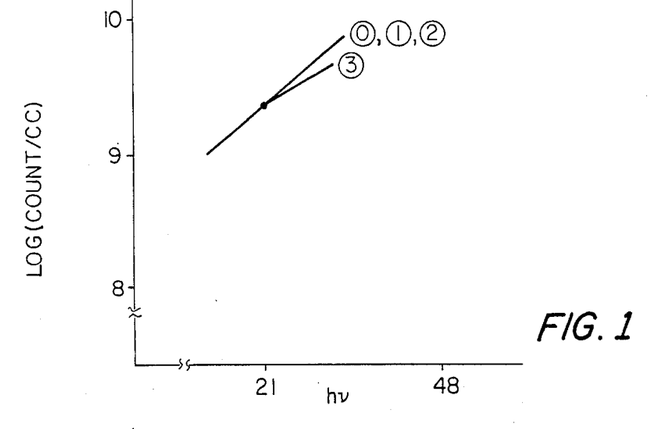
FIG. 1 depicts the case when a culture medium of high nutrition was used. No acceleration can be seen even though the substances containing S, N and C were added for the excitation of growth.
Figure 2:
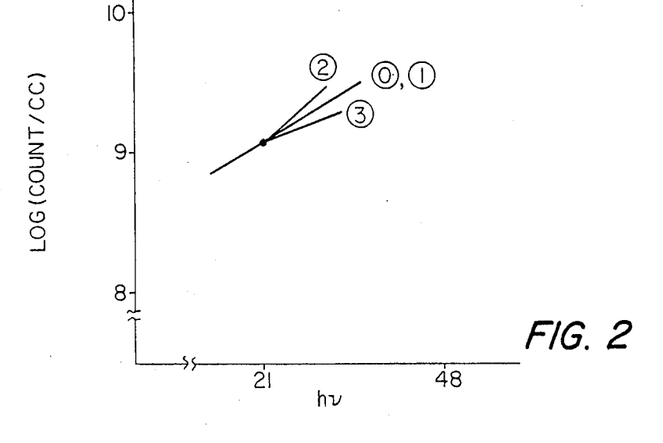
FIG. 2 depicts the case when a culture medium of medium nitrition was used. A faint tendency to accelerate the growth of bacteria can be seen as responding to the concentration of said substances added to the medium.
Figure 3:
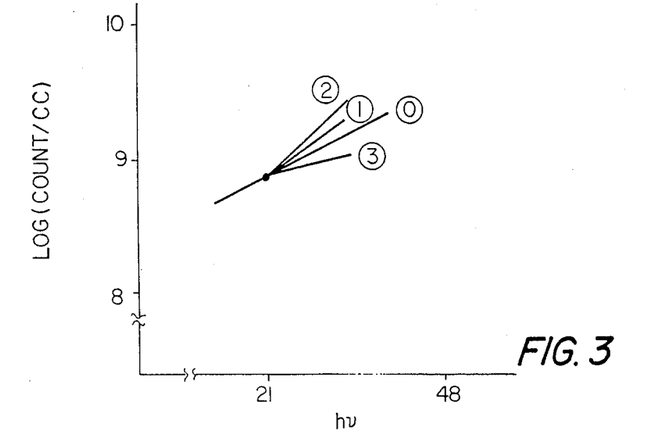
FIG. 3 depicts the case when a culture medium of low nutrition was used. A considerable acceleration of growth can be clearly seen, depending upon the concentration of said substances added to the medium.

FIG. 1 to FIG. 3 show some examples of such results obtained by the measurement with a nephelometer on those experiments concerning the acceleration of growth explained above. That is, adding S-, N- and C-containing substances into the basic culture medium in various concentrations at the period when the growth of bacteria entered the log phase, that is, after 21 hr from the beginning of cultivation in the basic medium, the response to the addition of those substances was accurately detected by the measurement of relative turbidity with the elapse of time, wherein ⓪was a case when the addition was not performed, ①was a case when Na$_2$S.9H$_2$O, NH$_3$ and acetic acid were added each in the amount of 0.1 g, ②was a case when those substances were added each in the amount of 1 g and ③ was a case when those were added each in the amount of 2 g. Upon the addition, 37% aqueous solution of ammonia was used as the source of NH$_3$ and glacial acetic acid was used as the source of acetic acid. By the way, in those experiments shown in FIG. 1–FIG. 3, the culture media used were (S−W) as a medium of low nutrition, (S−W)+1 g of casaminoacid +0.1 g of vitamin as a medium of middle nutrition and 10 g of peptone +5 g of gravy +5 g of NaCl+1 g of glucose as a medium of high nutrition, however, it should be pointed out that those compositions of culture media were only one example of culture experiments carried out by the present inventor.

TABLE 2

| Microscopic observation and Results of cultivation | F.R.I. No. 2546 | 2545 | 2544 | 2823 |
|---|---|---|---|---|
| Gram. dyeing | − | − | − | − |
| Shape | rod | short rod | rod | rod |
| Spore | − | − | − | − |
| Capsule | − | − | − | − |
| Motility | + | + | + | + |
| Condition for cultivation | facultative anaerobic | facultative anaerobic | facultative anaerobic | facultative anaerobic |
| Shape and appearance of colony (observed upon Japanese gelatin) | large circular type high upheaval wet smooth surface opaline wet circumference non-transparent, viscous | middle circular type low upheaval wet smooth surface opaline wet circumference semi-transparent, viscous | middle circular type semi-spherical upheaval wet smooth surface opaline wet circumference non-transparent, viscous | middle circular type semi-spherical upheaval smooth surface opaline wet circumference semi-transparent, viscous |
| Biochemical Properties | | | | |
| Generation of NH$_3$ | − | − | − | − |
| Generation of H$_2$S | − | − | − | − |
| Generation of indol | − | − | − | − |
| Production of catalase | − | − | − | − |
| Generation of coloring matter | − | − | − | − |
| Decomposition of urea | + | + | + | + |
| Utilization of citric acid | + | − | + | + |
| Liquidification of gelatin | + | − | − | − |
| V-P reaction | − | − | − | − |
| Reduction of nitrate | − | − | − | − |

Remark: + ... possitive, − ... negative

TABLE 3

| | | F.R.I. No. | | | |
|---|---|---|---|---|---|
| | | 2546 | 2545 | 2544 | 2823 |
| Decomposibility of saccharide | Glucose | + | + | + | + |
| | Starch | − | − | − | + |
| | Melizitose | − | − | − | − |
| | Maltose | − | − | − | − |

TABLE 3-continued

| | F.R.I. No. | | | |
|---|---|---|---|---|
| | 2546 | 2545 | 2544 | 2823 |
| Raffinose | − | − | − | − |
| Fluctose | ± | − | − | − |
| Melibiose | − | − | + | − |
| Xylose | − | ± | + | + |
| Sorbitol | − | − | − | − |
| Mannitol | − | − | − | − |
| Inositol | − | − | − | − |
| Arabinose | − | − | + | − |
| Lactose | − | − | − | − |
| Mannose | − | ± | − | + |
| Saccharose | − | − | − | − |
| Salicine | − | − | − | − |

TABLE 4

| Substance added to (S − W) culture medium | F.R.I. No. | | | |
|---|---|---|---|---|
| | 2546 | 2545 | 2544 | 2823 |
| none | ++ | ++ | ++ | ++ |
| S-containing amino-acid | +++ | ++ | ++ | +++ |
| Cyclic amino-acid | ++ | ++ | ++ | ++ |
| Amino-acid of chain structure | ++ | ++ | ++ | ++ |
| Cystine | +++ | ++ | ++ | +++ |
| Cysteine | +++ | ++ | ++ | +++ |
| Methionyl | +++ | ++ | ++ | +++ |
| Casamino-acid | +++ | +++ | +++ | +++ |
| Casamino-acid + Vitamin | +++ | +++ | +++ | +++ |
| Casamino-acid + Extract of yeast | +++ | +++ | +++ | +++ |
| Extract of yeast | +++ | +++ | +++ | +++ |
| Vitamins | ++ | ++ | ++ | ++ |

TABLE 5

| Substance added to basic medium | F.R.I. No. 2546 | | | | F.R.I. No. 2545 | | | | F.R.I. No. 2544 | | | | F.R.I. No. 2543 | | | |
|---|---|---|---|---|---|---|---|---|---|---|---|---|---|---|---|---|
| | a | b | c | d | a | b | c | d | a | b | c | d | a | b | c | d |
| none | − | | | | | − | + | | − | | | | − | | | |
| Acetic acid | − | | | | | − | + | | − | | | | + | | | |
| Butyric acid | | | | | | − | + | | − | | | | + | | | |
| Propionic acid | | | | | | − | + | | − | | | | + | | | |
| Na$_2$S.9H$_2$O | + | | | | | − | + | | − | | | | + | | | |
| Mercaptan | − | | | | | − | + | | − | | | | | | | |
| Ammonia | − | | | | | | | | − | | | | + | | | |
| Skatole | − | | | | | | + | | | | | | | | | |
| Extract of Excrement | | | | | | | | | | | | | | | | |

Remarks:
① The compositions of basic culture media were as follows;
a... [S-W] - glucose,
b... [S-W],
c... 8 g of pepton + 2 g of glucose,
d... 10 g of peptone + 5 g of gravy + 5 g of NaCl + 1 g of glucose.
② The weight of each substance added to a basic medium was 1 g/l of basic medium.
③ Those results shown in Table 4 and Table 5 were obtained by the observation with the naked eye.

Next, in Table 6, the experimental data on the specific growth rate ($\mu$) of two strains of bacteria when various kinds of basic culture media were used will be shown, wherein as one of them, a deodorization bacterium of the present invention, F.R.I. No. 2823 was chosen as a representative of the deodorization bacteria of the present invention and as other example of bacterium not belonging to the present invention, color bacillus was used for comparison with the former. According to the value of the specific growth rate $\mu$, from many experiments, it was found that, the $\mu$-value should be more than 0.65 in order to have a large ability for the deodorization when (S−W) is used for the basic culture medium.

TABLE 6

| | $\mu$-value | |
|---|---|---|
| Basic culture medium | F.R.I. No. 2823 | Colon bacillus |
| (S − W) − Glucose + F | 0.53 | — |
| (S − W) | 0.76 | 0.37 |
| (S − W) + Aminoi-acid having S | 0.82 | 0.41 |
| (S − W) + F | 0.82 | 0.41 |
| (S − W) + Amino acid + Vitamin | 0.85 | 0.46 |

The deodorization bacteria should have a large rate of growth as mentioned above, besides, it is necessary for the deodorization bacteria to show a resistance to the acid component of gall contained in the excrement, to various anti-bacterial agents, such as, for example, antibiotics and also to various spices contained in foods. Furthermore, it is desirable that the deodorization bacteria have an ability to resist to chemical reagents which have a deodorization ability in order to make it possible to use the deodorization bacteria together with those chemical reagents.

In Table 7, the results of the difference of the degree of deodorization due to the difference in sensibility to gall.

TABLE 7

| Sensibility of bacteria to gall | Change of residual smelling degree with elapse of time (F.R.I. No. 2823) | | |
|---|---|---|---|
| | 24 hrs | 48 hrs | 72 hrs |
| not sensitive | 0'~1 | 0' | 0~0' |
| sensitive | 3' | 3'~3 | 3 |

Next, the problems concerning subculturing will be described.

In the study on the deodorization using microorganisms, one difficult problem is to retain the deodorizing power of bacteria for a long period. In case of bacteria having a large ability for deodorization hitherto, it has been an inevitable tendency the deodorization ability of the bacteria to rapidly decrease with the elapse of time even though the most superior conventional techniques were employed for their maintenance.

Furthermore, the recovery of the deodorization ability of bacteria is a very difficult matter by any conventional technique or method if the original deodorization ability has been spoiled by performing a cultivation in an improper medium or by carrying out a repeated subculture. Thus, it becomes impossible to always get a highly effective result in a deodorization unless the establishment of a concrete culture conditions which makes it possible to keep the deodorizing power of bacteria constant for a long period, is realized. In other words, if a bacterial deodorizing agent is initially superior to a chemical one in deodorizing ability but is less stable, it will not be able to exhibit such superiority.

Hitherto, deodorizing agents consisting of microorganisms have encountered the situation mentioned above. Therefore, it was an urgent matter to find culture media which doesn't deteriorate the deodorizing power of superior bacteria and moreover, to develop culture media which are superior not only in keeping the deodorizing power but also in multiplication of target bacteria, itself.

The present inventor has made an extensive study on such problem mentioned above and has succeeded to finding the essential composition of a culture medium for the maintenance of the deodorizing power of bacteria during subculture. Thus, the present inventor has succeeded in attaining his object to develop culture media and moreover, has succeeded in isolating many deodorization bacteria. Here, the experimental results obtained by using five strains, that is, F.R.I. No. 2823, F.R.I. No. 3577, F.R.I. No. 3576, F.R.I. No. 3575 and F.R.I. No. 3578, which are typical strains among those isolated by the present inventor, will be disclosed. By the way, those five strains have a strong deodorization ability and each can simultaneously exhibit S-, N- and C-actions and in the testing them, since it was found that their activities were almost similar, the results will be shown depending upon the average values of the obtained data from them. In the experiment, the applied culture media contain 1% of a powder of gall. Further, the data shown in the following Table 8 of the present specification were obtained under the condition that each culture medium was added to the excrement in the amount of 10% in weight and the deodorization was carried out for 24 hr. at 28° C.

At first, for reference, an example of experimental results will be shown in Table 8-a, wherein deodorizing powers of those bacteria which were obtained by the sub-culture using conventional culture media of high to low nutrition. As is clearly shown from Table 8-a, a rapid decrease of activity of bacteria can never be presented if the sub-culture is carried out using any kind of conventional culture media.

TABLE 8-a

| Culture medium for sub-culture | Residual odor degree generation | | | |
|---|---|---|---|---|
| | 1st | 3rd | 5th | 7th |
| (A) Gravy + Peptone + Vitamins | 2' | 3 | 3' | 4 |
| (B) Gravy + Peptone | 2' | 3 | 3' | 4 |
| (C) Peptone + Vitamins | 2' | 3 | 3' | 4 |
| (D) Peptone | 2~2' | 3 | 3' | 4 |
| (E) Amino-acid + Vitamins | 2~2' | 3 | 3' | 3'~4 |
| (F) Amino-acid | 2 | 2' | 3 | 3' |
| (G) (S − W) + Vitamins | 1 | 1~1' | 2 | 3' |
| (H) (S − W) | 1' | 2 | 2' | 3' |

Next, in Table 8-b, the tendency of the decrease of activity is shown, wherein the sub-culture media whose compositions were respectively (A), (B), (C) ... and (H) shown in Table 8-a, further contain 1 g/l of F component were used for the sub-culture. Here the F component is the general name of S-containing compounds + N-containing compounds + C-containing compounds, each having a foul smelling tendency, which are contained in the excrement and practically, in those experimental tests shown in Table 8-b, $Na_2S \cdot 9H_2O$, $NH_3$ and acetic acid were used as the representative of those S-, N- and C-compounds.

TABLE 8-b

| Culture medium for sub-culture | Residual odor degree generation | | | |
|---|---|---|---|---|
| | 1st | 3rd | 5th | 7th |
| (A) + F | 2 | 2' | 3 | 3' |
| (B) + F | 2 | 2' | 3 | 3' |
| (C) + F | 1'~2 | 2 | 2' | 3 |
| (D) + F | 1'~2 | 2 | 2' | 3 |
| (E) + F | 1'~2 | 2 | 2' | 2'~3 |
| (F) + F | 1'~2 | 2 | 2' | 3 |
| (G) + F | 1 | 1~1' | 1' | 1' |
| (H) + F | 1 | 1' | 1'~2 | 2 |

As is clearly understood from Table 8-a and Table 8-b, there exist suitable compositions for culture media in the vicinity of the region near (G) and (H) or (G)+F and (H)+F where the decrease of activity is rather small.

Next, in the vicinity of the said region near to the compositions (G), (H), (G)+F and (H)+F where the decrease of activity was observed to be small, an experiment was repeated eliminating the glucose component from the composition of the (S−W) medium and the results were shown in the following table, wherein —glucose means the glucose component was eliminated.

| Culture medium for sub-culture | Residual odor degree generation | | | |
|---|---|---|---|---|
| | 1st | 3rd | 5th | 7th |
| (G) − glucose | 1 | 1 | 1' | 1' |

-continued

| Culture medium for sub-culture | Residual odor degree generation | | | |
|---|---|---|---|---|
| | 1st | 3rd | 5th | 7th |
| (H) − glucose | 1 | 1~1' | 1'~2 | 2 |
| (G) − glucose + F | 0'~1 | 0'~1 | 0'~1 | 0'~1 |
| (H) − glucose + F | 0'~1 | 1 | 1~1' | 1' |

As is understood from the above table, the important factors for the composition of culture medium to prevent the decrease of deodorizing power of those five strains of bacteria are, firstly, the basic medium should be poor in its nutritive state and moreover, secondly, it should contain F substances and vitamin as additive components to the culture medium.

Next, in Table 9-a and Table 9-b, the results on two series of experiments are summarized, wherein the activities of bacteria multiplied successively by repeated subculture using culture media whose basic composition was (G)-glucose were examined or (H)-glucose and, also the effect of addition of various amino-acids was examined.

TABLE 9-a

| Amino-acid added to basic culture medium consisting of (G)- glucose for sub-culture | residual smell generation | |
|---|---|---|
| | 4th | 11th |
| Cystine | 0'~1 | 1 |
| Cysteine | 1 | 1' |
| Methionine | 0'~1 | 1 |
| Glycine | 1 | 2 |
| Glutamic acid | 1 | 2 |
| Arginine | 2 | 2' |
| Asparagine | 2 | 2' |
| Aspartic acid | 2 | 2' |
| Alanine | 1' | 2 |
| Phenyl alanine | 2 | 2' |
| Amino-butylic acid | 1' | 2' |
| Leucine | 2' | 3 |
| Isoleucine | 2' | 3 |
| Proline | 2 | 2' |
| Lysine | 1' | 2 |
| tryrosine | 1' | 2' |
| Histidine | 1 | 2' |
| Tryptophin | 2 | 3 |
| Threonine | 2 | 3 |
| Serine | 2 | 3 |
| Casamino-acid | 1'~2 | 2~2' |

TABLE 9-B

| Amino-acid added to basic culture medium consisted of (H)- glucose for subculture | Residual smell generation | |
|---|---|---|
| | 4th | 11th |
| Cystine | 1~1' | 1'~2 |
| Cysteine | 1~1' | 2 |
| Methionine | 1~1' | 2 |
| Glycine | 1' | 2 |
| Glutamic acid | 1' | 2' |
| Arginine | 2~2' | 3 |
| Asparagine | 2' | 3 |
| Aspartic acid | 2' | 3 |
| Alanine | 2 | 2' |
| Phenylalanine | 2' | 3 |
| Amino-butyric acid | 2 | 2'~3 |
| Leucine | 3 | 3' |
| Isoleucine | 3 | 3' |
| Proline | 2' | 3 |
| Lysine | 1' | 2' |
| Tyrosine | 1'~2 | 2' |
| Histidine | 1~1' | 2' |
| Tryptophan | 2~2' | 3~3' |
| Threonine | 2~2' | 3~3' |

TABLE 9-B-continued

| Amino-acid added to basic culture medium consisted of (H)-glucose for subculture | Residual smell generation | |
|---|---|---|
| | 4th | 11th |
| Serine | 2~2' | 3~3' |
| Casamino-acid | 2 | 2' |

In the following Table 10-a and Table 10-b, the results of two series of experiments are summarized, where the activities of bacteria multiplied successively in the repeated subculture using culture media whose basic component was (G)-glucose or (H)-glucose and, further, where various amino-acids the foul smelling component F, were added.

TABLE 10-a

| | Substance added to basic culture medium consisting of (G)-glucose for sub-culture | residual smell generation | |
|---|---|---|---|
| | | 4th | 11th |
| | Cystine | 0'~1 | 0'~1 |
| | Cysteine | 0'~1 | 0'~1 |
| | Methionine | 0'~1 | 0'~1 |
| | Glycine | 0'~1 | 1 |
| | Glutamic acid | 0'~1 | 1 |
| F | Agrinine | 1 | 1' |
| foul smelling | Asparagine | 1 | 1' |
| component | Asparatic acid | 1 | 1' |
| | Alanine | 0'~1 | 1'~1 |
| + | Phenyl alanine | 1 | 1' |
| | Amino-butyric acid | 0'~1 | 1' |
| | Leucine | 1 | 1'~2 |
| | Isoleucine | 1 | 1'~2 |
| | Proline | 1 | 1' |
| | Lysine | 0'~1 | 1 |
| | Tyrosine | 0'~1 | 1' |
| | Histidine | 0'~1 | 1'~1 |
| | Tryptophan | 1 | 1'~2 |
| | Theronine | 1 | 1'~2 |
| | Serine | 1 | 1'~2 |
| | Casamino-acid | 0'~1 | 1'~1 |

TABLE 10-b

| | Substance added to basic culture medium consist 10 g of (H)—glucose for sub-culture | residual smell generation | |
|---|---|---|---|
| | | 4th | 11th |
| | Cystine | 1 | 1' |
| | Cysteine | 1 | 1' |
| | Methionine | 1 | 1' |
| | Glycine | 1 | 1' |
| | Glutamic acid | 1 | 1' |
| F | Arginine | 1~1' | 1'~2 |
| foul-smellint | Asparagine | 1' | 2 |
| component | Asparlic acid | 1' | 2 |
| | Alanine | 1~1' | 2 |
| + | Phenyl alanine | 1' | 2 |
| | Amino-butyric acid | 1~1' | 2 |
| | Leucine | 1' | 2 |
| | Isoleucine | 1' | 2 |
| | Proline | 1' | 2 |
| | Lysine | 1 | 1' |
| | tryrosine | 1~1' | 1' |
| | Histidine | 1 | 1'~2 |
| | Triptophan | 1' | 2 |
| | Threonine | 1' | 2 |
| | Serine | 1' | 2 |
| | Casamino-acid | 1~1' | 1'~2 |

As it is clearly understood from Table 9 and Table 10, amino-acids which are effective to keep the deodorizing power of the bacteria at almost constant level for many generations are cystine, cysteine, methionine, glycine, glutamic acid, amino-butyric acid, lysine, histidine, alanine, cytosinetyrosine, etc. and other amino-acids used in those experiments can not prevent a gradual decrease of the deodorizing power of the bacteria.

Further experiments on the bacteria cultivated by the successive sub-culture proved that further addition of starch, mineral materials, etc. has a remarkable effect on the preservation of deodorizing power. Furthermore, it was more beneficial to add any combination of starch, mineral, vitamin and amino acid which was proved to be effective, such as cystine, etc., to the said culture media for the preservation of deodorizing power and such an addition was also effective to increase the rate of growth. These effects mentioned above can be clearly understood from Table 11–Table 13.

TABLE 11

| Substance added to (G)—glucose + F | Residual odor degree generation | | | |
|---|---|---|---|---|
| | 10th | 15th | 20th | 25th |
| Starch | 0'~1 | 0'~1 | 1 | 1 |
| Mineral | 0'~1 | 1 | 1 | 1~1' |
| Starch + Mineral | 0'~1 | 0'~1 | 0'~1 | 0'~1 |

TABLE 12

| Substance added to basic culture medium # | Number of bacteria (aerobic) cultured for 72 hrs at 28° C. | Residual odor degree (15th generation) |
|---|---|---|
| none | 5 × 10⁹ | 2' |
| Starch | 7 × 10⁹ | 1'~2 |
| Mineral | 6 × 10⁹ | 2 |
| Vitamins | 7 × 10⁹ | 1' |
| Starch + Mineral | 12 × 10⁹ | 1~1' |
| Starch + Vitamins | 13 × 10⁹ | 1 |
| Mineral + Vitamins | 8 × 10⁹ | 1~1' |
| Starch + Mineral + Vitamins | 15 × 10⁹ | 0'~1 |

Remark: The basic culture medium was (S–W) - glucose + F

TABLE 13

| Substance added to basic culture medium [(G)—glucose + F] | Residual odor degree generation | | | |
|---|---|---|---|---|
| | 20th | 25th | 30th | 35th |
| Starch + Mineral | 0'~1 | 0'~1 | 1 | 1 |
| Starch + Mineral + Cystine | 0'~1 | 0'~1 | 0'~1 | 0'~1 |

Next, the present inventor also studied the problem concerning the storage of bacteria, that is, various conditions were applied to bacteria in a dry, semi-dry and wet state to determine the change of their activity and the inventor has come to a conclusion that it is almost impossible to carry out a storage of bacteria for a considerable long period without spoiling their activity so as it can be called as "storage of commercial product" from the commercial stand point unless bacteria are put in a dry state.

Hereafter, experimental data which forced the inventors to have such a conclusion mentioned above, will be explained in a proper order. At first, Table 14 will be shown. Those data in Table 14 were obtained using bacteria F.R.I. No. 2823 as a test sample, however, it was also confirmed that analogous data can be obtained even if other bacteria are chosen as a test sample and unfortunately, no exception was found.

TABLE 14

| State of bacteria during storage | Coating material | Allowable period of storage 28° C. | 8° C. |
|---|---|---|---|
| dry | — | 7 days | 20 days |
| semi-dry | — | 5 days | 15 days |
| wet | — | 3 days | 7 days |
| Co-existed with liquor | — | 2~3 days | 5 days |

In Table 14, the dry state of bacteria means the bacteria is in a state where the content of water is 8%, wherein the drying of bacteria can be carried out by a conventional technique, the semi-dry state means the bacteria contains 15% of water, the wet state means a state of bacteria gathered from the culture medium, which is referred to wet cake and the state of bacteria co-existing with liquor means the state of culture medium itself after the end of cultivation. The allowable period of storage means the longest period of storage during it the bacteria can be stored without decreasing their deodorizing power.

In the above experiment, in order to find suitable storage conditions which can be commercially used, the water content and the temperature were varied but, it was impossible to prevent the decrease of deodorizing power for an appreciable period. However, since S-, N- and C-containing compounds are very effective for the prevention of the decrease of deodorizing power of bacteria and also for their rapid growth in the successive sub-culture as explained already, it was thought that the existence of such compounds around the body of bacteria may help prevent the decrease of their activity. Coating tests were carried out, while adjusting the water content of bacteria to various degrees, at the same time.

Table 15 shows the results of such test on bacteria coated with substances which played an important role in their successive sub-culture.

TABLE 15(a)

| State in storage | Coating material | Allowable period of storage 28° C. | 8° C. |
|---|---|---|---|
| dry | S—, N—and C—containing compounds | 25 days | 120 days |
| | Mineral | 10 days | 40 days |
| | Vitamins | 15 days | 50 days |
| | Starch | 20 days | 100 days |
| | Cystine | 20 days | 100 days |
| | Glutamic acid | 20 days | 100 days |
| wet | S—, N—, C—containing compounds | 5 days | 25 days |
| | Mineral | 4 days | 15 days |
| | Vitamins | 4 days | 20 days |
| | Starch | 4 days | 25 days |
| | Cystine | 4 days | 25 days |
| | Glutamic acid | 4 days | 25 days |
| liquid | S—, N—, C—containing compounds | 4 days | 20 days |
| | Mineral | 3 days | 12 days |
| | Vitamins | 3 days | 12 days |
| | Starch | 3 days | 20 days |
| | Cystine | 3 days | 20 days |
| | Glutamic acid | 3 days | 20 days |

In Table 15(a), (b), the coating of the body of bacteria in the liquid state means that each coating material was added into the culture medium and intimately mixed, and then the mixture was allowed to stand for storage. Further, the length of the allowable period of storage differed considerably in accordance with the difference of the concentration of coating material and there existed an optimum concentration for the period of storage as shown in Table 15(b). The data on the allowable period of storage shown in Table 15(a) are those values obtained by the test on bacteria F.R.I. No. 2823 coated with each coating material of the optimum concentration. The situation is the same also on those data which appear in Table 16 and Table 17.

TABLE 15 (b)

| Strain (F.R.I. No.) | State in Storage | Coating Material | Concentration (d) | Allowable Period of Storage 28° C. | 8° C. |
|---|---|---|---|---|---|
| 2823 | liquid | S—, N—, C— containing compounds | 1 | 2 days | 10 days |
| | | | 5 | 3 days | 15 days |
| | | | 10 | 3 days | 20 days |
| | | | 20 | 4 days | 20 days |
| | | Cystine | 1 | 2 days | 10 days |
| | | | 5 | 2 days | 15 days |
| | | | 10 | 3 days | 20 days |
| | | | 20 | 3 days | 20 days |
| 2544 | liquid | S—, N—, C— containing compound | 1 | 2 days | 10 days |
| | | | 5 | 3 days | 15 days |
| | | | 10 | 4 days | 20 days |
| | | | 20 | 3 days | 12 days |
| | | Cystine | 1 | 2 days | 10 days |
| | | | 5 | 3 days | 15 days |
| | | | 10 | 4 days | 20 days |
| | | | 20 | 3 days | 12 days |
| 2545 | liquid | S—, N—, C—, containing compounds | 1 | 3 days | 15 days |
| | | | 5 | 4 days | 20 days |
| | | | 10 | 2 days | 10 days |
| | | | 20 | 1 day | 7 days |
| | | Cystine | 1 | 3 days | 15 days |
| | | | 5 | 4 days | 20 days |
| | | | 10 | 3 days | 12 days |
| | | | 20 | 2 days | 7 days |
| 2546 | liquid | S—, N—, C— containing compounds | 1 | 4 days | 20 days |
| | | | 5 | 3 days | 15 days |
| | | | 10 | 1 day | 6 days |
| | | | 20 | 1 day | 5 days |
| | | Cystine | 1 | 4 days | 20 days |
| | | | 5 | 4 days | 15 days |

TABLE 15 (b)-continued

| Strain (F.R.I. No.) | State in Storage | Coating Material | Concentration (d) | Allowable Period of Storage 28° C. | 8° C. |
|---|---|---|---|---|---|
| | | | 10 | 2 days | 10 days |
| | | | 20 | 1 day | 5 days |

Remarks:
①  The concentration, d in the table, was defined as follows; 1d means the liquid state contains 0.1% of each of $Na_2S.9H_2O$, ammonia and acetic acid in weight.
② The concentration of cystine, d in the table was also defined as follows; 1d means the liquid state contains 0.1% of cystine in weight.

Table 16 shows the results of storage of the said bacteria, wherein each bacteria sample was coated with a material which is shown to play a significant role in accelerating the decrease of deodorizing power of the bacteria in the successive sub-culture.

TABLE 16

| State in storage | Coating material | Allowable period of storage (days) 28° C. | 8° C. |
|---|---|---|---|
| dry | Peptone | 5 | 15 |
| | Gravy | 7 | 20 |
| | Tryptophan | 6 | 20 |
| | Serine | 7 | 20 |
| wet | Peptone | 2 | 5 |
| | Gravy | 2 | 5 |
| | Tryptophan | 2 | 5 |
| | Serine | 2 | 7 |
| liquid | Peptone | 2 | 5 |
| | Gravy | 2 | 4 |
| | Tryptophan | 2 | 5 |
| | Serine | 2 | 5 |

As it is understood from above tables, it is effective to coat the body of bacteria with a substance which contributes to the original deodorization ability in the sub-culture. Thus, it can be concluded that a substance which contributes to maintaining the original deodorization ability of bacteria in a sub-culture also plays an important role in the preservation of that ability during storage.

With such information on the coating material, further tests were carried out to find better coating materials by the combination of those coating materials which showed superiority and the present inventor has discovered that it is very effective to coat the body of bacteria with a combination of those materials which compose a superior culture medium or a combination of S-, N- and C-containing compounds and/or starch and/or vitamin+mineral or a combination of aminoacids which are effective for the preservation of deodorizing power or again a proper mixture of those combinations, each material being employed in an appropriate combination. Table 17(a) shows three examples of coating materials.

TABLE 17 (a)

| State in storage | Coating material | Allowable period of storage 28° C. | 8° C. |
|---|---|---|---|
| dry | A ... (S-W) - Glucose + F + Starch + Mineral + Vitamins | 60 days | 300 days |
| | B ... Cystine + Cystein + Methionine | 40 days | 200 days |
| | C ... S—, N—, C—comps + Starch + Mineral + Vitamins | 60 days | 300 days |
| wet | A | 8 days | 60 days |
| | B | 7 days | 50 days |
| | C | 7 days | 50 days |

TABLE 17 (a)-continued

| State in storage | Coating material | Allowable period of storage 28° C. | 8° C. |
|---|---|---|---|
| liquid | A | 6 days | 60 days |
| | B | 5 days | 50 days |
| | C | 5 days | 50 days |

Here, another example will be shown. The data shown in Table 14 to Table 17(a) for storage test were obtained by sealing nitrogen gas into the vapour phase of each sample, however, other gases can be effectively used. The effect of various gases such as $CO_2$, $O_2$, $H_2$, methane gas and air on the allowable period of storage are shown in Table 17(b), together with that of nitrogen gas. From this data, it can be understood that $CO_2$ and $H_2$ are very superior to use for storage almost comparably to nitrogen gas, however, air and methane gas are slightly inferior and oxygen gas is most inferior.

TABLE 17 (b)

| State in storage | Coating material | Gas sealed | Allowable period or storage 28° C. | 8° C. |
|---|---|---|---|---|
| dry | [A] | $N_2$ | 60 days | 300 days |
| | | $CO_2$ | 60 days | 300 days |
| | | $O_2$ | 15 days | 50 days |
| | | $H_2$ | 55 days | 250 days |
| | | Methane gas | 40 days | 200 days |
| | | Air | 30 days | 100 days |
| dry | [B] | $N_2$ | 40 days | 200 days |
| | | $CO_2$ | 40 days | 200 days |
| | | $O_2$ | 12 days | 40 days |
| | | $H_2$ | 40 days | 200 days |
| | | Methane gas | 30 days | 150 days |
| | | Air | 20 days | 70 days |
| dry | [C] | $N_2$ | 60 days | 300 days |
| | | $CO_2$ | 60 days | 300 days |
| | | $O_2$ | 15 days | 50 days |
| | | $H_2$ | 55 days | 250 days |
| | | Methane gas | 40 days | 180 days |
| | | Air | 30 days | 100 days |

The following conclusion can be derived from those experiments mentioned above.

(a) As the temperature for the preservation of deodorization ability of bacteria, 8° C. is more desirable than 28° C. (the allowable period of storage at 8° C. is about five times of that at 28° C.).

(b) As to the state of bacteria during storage, both the wet state and also the state co-existant with the culture medium (sometimes, this state was called as the liquid state in short) are not desirable.

(c) There exists an optimum concentration of coating material characteristic to the species of strain.

(d) If bacteria are put in the dry state, coated with a proper coating material, it is possible to store them for a long period.

(e) A desirable coating material can be selected depending upon the application of bacteria. For example, in case of bacteria used as a deodorizing agent by oral administration, a combination of amino-acid, vitamin, mineral and starch is proper for the coating material, avoiding the use of S-, N- and C-compounds.

(f) There exists an intimate relation between the coating material and the components of the culture medium, which is effective to keep original deodorizing power.

Furthermore, in order to practically employ a deodorant consisting of bacteria, another important problem to be solved is the selection of a single strain of as small a number of strains as possible. There are many workers who are engaging in the study on the method of deodorization using bacteria of many strains. However, it is a difficult matter from a practical standpoint to keep the deodorizing power of bacteria of many strains at a constant level and to produce a commercial product having a stable and constant quality. Moreover, it is almost impossible to prove the non-pathogenicity of bacteria of many strains, separately and in combination. Moreover, it should be noted that by the use of such a deodorant comprising many strains the possibility of an irremedial breakdown of the natural biobalance exists.

From the viewpoint mentioned above, it is clear that bacteria of single strain is most desirable to use. Even if such a species of bacteria is difficult to obtain, it is a matter of necessity to use as small a number of strains as possible such as 2–3 strains. Fortunately, the present inventors have succeeded isolating various strains which can be used solely or as a mixture of two or three of them for deodorization. Surely, this has an important meaning on the practical use of bacteria for deodorization. Furthermore, the inventor has succeeded in carrying out the development of two subjects which are necessary for the practical use of bacteria. One of them is as follows.

When a single strain of bacteria which exhibits rapid growth in the aerobic condition is isolated or in the facultative anaerobic condition, it seems to be almost impossible to achieve growth in the anaerobic condition. The importance of rapid growth in the anaerobic condition for the present purpose has already been pointed out in this specification. For more than one year, the inventor endeavoured to selectively acclimatize such bacterial to the anaerobic condition which appears very often in the deodorization, and succeeded, to get bacteria of single strain which can growth rapidly in the anaerobic condition and also have a superior deodorization ability. The degree of multiplication of the bacteria just after the isolation into single strain and that of the bacteria after being acclimatized to the anaerobic condition in the anaerobic cultivation are shown in Table 18.

TABLE 18

| Culture medium | Count of bacteria (F.R.I. No. 2823)/cc after an anaerobic culture at 28° C. for 72 hr. | |
|---|---|---|
| | Strain just after isolation | Strain acclimatized |
| S-W —glucose + F | $1 \times 10^8$ | $3 \times 10^9$ |
| S-W | $5 \times 10^8$ | $5 \times 10^9$ |
| S-W + Amino acid + Vitamins | $1 \times 10^9$ | $10 \times 10^9$ |

The other important development made by the inventor is the acclimatization of bacteria to a given temperature situated in a broad range of temperature. This necessity, of course, comes from the fact that the deodorization bacteria will be used broadly everywhere in the world, such as, from the tropical zone to subtropical zone, temperate zone and frigid zone. Thus, the bacteria of single strain are desired to have a considerably large rate of growth and also a strong deodorizing power even at a high temperature or at a low temperature. If the temperature range represented by typical three temperatures such as $+8°$ C., $+28°$ C. and $+40°$ C. and the conditions of partial pressure of oxygen are classified into three types, that is, aerobic, facultative anaerobic and anaerobic. 9 conditions appear as shown in the following table. To those conditions, the bacteria of single strain should be acclimatized in order to response to the demand.

| | +8° C. | +28° C. | +40° C. |
|---|---|---|---|
| aerobic | o | o | o |
| facultative anaerobic | o | o | o |
| anaerobic | o | o | o |

Starting from a strain which exhibited rapid growth at 28° C. in the aerobic or facultative anaerobic condition, a selective acclimatization to each of those 9 given conditions was carried out repeatedly for a long period and at last, the present inventor has succeeded in cultivating them.

The degrees of multiplication of those acclimatized bacteria and the degree of multiplication of the single original strain obtained by the isolation and used as the starting material for the acclimatization to the nine given conditions concerning the temperature and the partial pressure of oxygen, are listed in Table 19.

TABLE 19

| Partial pressure of oxygen | Count of bacteria/cc | | | | | |
|---|---|---|---|---|---|---|
| | Strain just after isolation | | | Strain acclimatized | | |
| | 8° C. | 28° C. | 40° C. | 8° C. | 28° C. | 40° C. |
| aerobic | $1 \times 10^8$ | $8 \times 10^9$ | — | $2 \times 10^9$ | $10 \times 10^9$ | $8 \times 10^9$ |
| facultative anaerobic | $3 \times 10^7$ | $5 \times 10^9$ | — | $1 \times 10^9$ | $8 \times 10^9$ | $6 \times 10^9$ |
| anaerobic | $1 \times 10^6$ | $1 \times 10^8$ | — | $3 \times 10^8$ | $5 \times 10^9$ | $3 \times 10^9$ |

Remarks:
1 The culture medium was (S-W) and each cultivation was carried out for 72 hr.
2 The strain used for the acclimatization was the same as to that in Table 18.

During those experiments, it was found that the adaptability of bacteria to the culture condition is rather much different from strain to strain, that is, there exists strain which easily adapt to the culture condition and on the other hand, which has a strong inertia to adapt to the applied condition.

At any rate, the increase of the number of species of strains such as, for example, to nine as in the above experiment makes it very complicated to carry out the experimental work since it is always necessary to keep the deodorizing power of bacteria of single strain at a high level. However, by the cultivation of various bacteria of single strain which can adapt to the climatic condition such as temperature and also partial pressure of oxygen in the medium where the bacteria are desired to growth, it has become possible to carry out the deodorization everywhere in the world by a proper selection of the deodorization bacteria developed by the present inventor. An example to prove what mentioned above is shown in Table 20.

TABLE 20

| Experimental condition (excrement) | | Residual odor degree (deodorizing power test) | |
|---|---|---|---|
| | | Strain original | Strain acclimatized |
| bacteria were added to a receiver of excrement in a basin | during spring | 3 | 1' |
| | during summer | 3' | 1' |
| | during autumn | 3 | 1' |
| | during winter | 4 | 1' |
| | 8° C. | 2' | 1 |
| | 28° C. | 1 | 0'~1 |
| | 40° C. | 4 | 0'~1 |

Remarks:
1 The original strain not acclimatized was just as that shown in Table 18.
2 The acclimatized strains were chosen from those shown in Table 19.
3 The value of residual odor during one season is the mean value during it.

What is claimed is:

1. A method for culturing a living, autotrophic bacteria for the deodorization of excrement which comprises culturing said bacteria in a medium comprising said excrement containing one or more S-, N- and C-containing compounds which are present as foul-smelling substances in said excrement and/or an amino acid selected from the group consisting of cystine, cysteine, methionine, glycine, glutamic acid, alanine, aminobutyric acid, lysine, trysosine and histidine, said culturing being conducted for a time and under conditions to effect multiplication of the autotrophic bacteria sufficient to provide deodorization of said excrement, wherein said one or more S-, N- and C-containing compounds and/or amino acids are present in an amount sufficient to accelerate the rate of growth of the bacteria when they enter logarithmic phase relative to the rate of growth in the absence of said S-, N- and C-containing compounds and/or amino acids.

2. A method for culturing as claimed in claim 1, wherein said medium further comprises one or more starches, one or more vitamins and/or one or more minerals.

3. A deodorant composition capable of deodorizing excrement comprising (I) a deodorizing effective amount of at least one up to a number of strains of an autotrophic bacteria such that the cumulative deodorizing effect of said strains comprises N-, C- and S-action, said bacterial strain(s) exhibiting a $\mu$ value of 0.25 more than that exhibited by colon bacteria in an S—W medium having the composition consisting of 1 g of $KH_2PO_4$, 0.7 g of $MgSO_4.7H_2O$, 1 g of NaCl, 4 g of $(NH_4)_2PHO_4$, 0.03 g of $FeSO_4.7H_2O$ and 5 g of glucose; said at least one bacterial strain, or said number of strains in combination, exhibiting accelerated growth in said S—W medium in the presence of (a) each of $Na_2S.9H_2O$, ammonia and a lower aliphatic carboxylic acid and/or (b) at least one of cystine, cysteine, and methionine and (II) a protective coating substance for said bacteria.

4. The deodorant composition of claim 3, wherein said at least one up to a number of bacterial strains exhibit(s) a resistance to gall in a concentration of 1% or more.

5. The deodorant composition of claim 4, wherein said bacterial composition contains at least one strain exhibiting an S-action as determined by ability to show an accelerated growth in the presence of sodium sulfide and an ability to change the sodium sulfide into completely odorless material, at least one strain exhibiting an N-action as determined by ability to show an accelerated growth in the presence of ammonia, indole or skatole and an ability to change them into completely odorless material, and at least one strain exhibiting a C-action as determined by ability to show an accelerated growth in the presence of a lower aliphatic carboxylic acid and an ability to change said acid into completely odorless material.

6. The deodorant composition of claim 4, wherein said bacterial composition contains at least a set of two strains as set forth below:
   (a) one exhibiting S- and N-actions, and the other exhibiting C-action;
   (b) one exhibiting N- and C-actions, and the other exhibiting S-action; or
   (c) one exhibiting C- and S-actions, and the other exhibiting N-action.

7. The deodorant composition of claim 4, wherein said bacterial composition contains at least one strain exhibiting each of S-, N- and C-actions.

8. The deodorant composition of claim 4, wherein said at least one up to a number of bacterial strain(s) is or are a strain or strains subcultured in a subculturing medium containing (A) at least one S-, N- or C-containing compound present in excrement as a foul-smelling substance, and/or (B) at least one S-containing amino acid, said at least one S-, N-, or C-containing compound and/or at least one amino acid being present in an amount sufficient to maintain the deodorizing power during subculturing.

9. The deodorant composition of claim 8, wherein said subculturing medium further comprises one or more starches, one or more minerals and/or one or more vitamins.

10. The deodorant composition according to claim 9, wherein said at least one up to a number of bacterial strains is or are bacterial strain(s) acclimatized to exhibit aerobic, facultative anaerobic or anaerobic properties.

11. The deodorant composition of claim 8, wherein said at least one up to a number of strains is or are strain(s) stored at a temperature of 8° C.

12. The deodorant composition of claim 8, wherein said at least one up to a number of bacterial strain(s) is or are strain(s) stored in an inert gas.

13. The deodorant composition in claim 12 wherein said inert gas is $CO_2$, $N_2$, $H_2$ or He.

14. The deodorant composition according to claim 3, wherein the at least one up to a number of bacterial strains is or are bacterial strain(s) acclimatized to grow at temperatures within the range of +8° C. to 40° C.

15. The deodorant composition according to claim 3, wherein the at least one up to a number of bacterial strain(s) exhibit(s) resistance to anti-bacterial agents and condiments.

16. A bacterial preparation comprising in admixture: (I) a bacterial composition comprising a deodorizing effective amount of at least one up to a number of strains of an autotrophic bacteria such that the cumulative deodorizing effect of said strain(s) comprises N-, C-and S-action, said bacterial strain(s) exhibiting a $\mu$ value of 0.25 or more than that exhibited by colon bacteria in an S—W medium having the composition consisting of 1 g of $KH_2PO_4$, 0.7 g of $MgSO_4.7H_2O$, 1 g of NaCl, 4 g of $(NH_4)_2PO_4$, 0.03 g of $FeSO_4.7H_2O$ and 5 g of glucose; said at least one bacterial strain, or said number of strains in combination, exhibiting accelerated growth in said S—W medium in the presence of (a) each of $Na_2S.9H_2O$, ammonia and a lower aliphatic carboxylic acid and/or (b) at least one member selected from the group consisting of cystine, cysteine, and methionine and (II) a composition comprising (A) at least one of S-, N- and C-compounds present in excrement as foul-smelling substances and/or (B) at least one compound selected from the group consisting of an S-containing amino acid, glycine, glutamic acid, alanine, aminobutyric acid, lysine, tyrosine and histidine, said at least one S-, N- and C-containing compound and/or at least one amino acid being present in an amount sufficient to maintain deodorizing power during subculturing.

17. The bacterial preparation of claim 16, wherein said at least one up to a number of bacterial strains exhibit(s) a resistance to gall in a concentration of 1% or more.

18. The bacterial preparation of claim 16, wherein said composition (II) further comprises one or more starches, one or more minerals, and/or one or more vitamins.

19. The bacterial preparation of claim 17 or claim 18, wherein said bacterial composition contains at least one strain exhibiting an S-action as determined by ability to show an accelerated growth in the presence of sodium sulfide and an ability to change the sodium sulfide into completely odorless material, at least one strain exhibiting an N-action as determined by ability to show an accelerated growth in the presence of ammonia, indole or skatole and an ability to change them into completely odorless material, and at least one strain exhibiting a C-action as determined by ability to show an accelerated growth in the presence of a lower aliphatic carboxylic acid and an ability to change said acid into completely odorless material.

20. The bacterial preparation of claim 17 or claim 18, wherein said bacterial composition contains at least a set of two strains as set forth below;
   (a) one exhibiting S- and N-actions, and the other exhibiting C-action;
   (b) one exhibiting N- and C-actions, and the other exhibiting S-action; or
   (c) one exhibiting C- and S-actions, and the other exhibiting N-action.

21. The bacterial preparation of claim 17 or claim 18, wherein said bacterial composition contains at least one strain exhibiting each of S-, N- and C-actions.

22. The bacterial preparation of claim 17 or claim 18, wherein said at least one up to a number of bacterial strain(s) is or are a strain or strains subcultured in a subculturing medium containing (A) at least one of S-, N- and C-containing compounds present in excrement as foul-smelling substances and/or (B) at least one S-containing amino acid, wherein said at least one S-, N- and C-containing compound and/or at least one amino acid is present in an amount sufficient to maintain the deodorizing power during subculturing.

23. The bacterial preparation of claim 22, wherein said subculturing medium further comprises at least one or more starches, one or more minerals and/or one or more vitamins.

24. The bacterial preparation of claim 17 or claim 18, wherein said at least one up to a number of strains is or are strain(s) stored at a temperature of 8° C.

25. The bacterial preparation of claim 17 or claim 18, wherein said at least one up to a number of bacterial strain(s) is or are strain(s) stored in an inert gas.

26. The bacterial preparation of claim 25 wherein said inert gas is He.

27. The bacterial preparation of claim 17 or claim 18, wherein said at least one up to a number of bacteria strains is or are bacteria strain(S) acclimatized to exhibit aerobic, facultative anaerobic or anaerobic properties.

28. The bacterial preparation of claim 17 or claim 18, wherein the at least one up to a number of bacteria strains is or are bacteria strain(s) acclimatized to grow at temperatures within the range of +8° C. to 40° C.

29. The bacterial preparation of claim 17 or claim 18, wherein the at least one up to a number of bacteria strains exhibit(s) resistance to anti-bacterial agents and condiments.

* * * * *